United States Patent [19]

Yoshida et al.

[11] Patent Number: 5,266,728
[45] Date of Patent: Nov. 30, 1993

[54] METHOD FOR PRODUCING OPTICALLY ACTIVE 3-SUBSTITUTED-2-NORBORNANONES AND THEIR INTERMEDIATES

[75] Inventors: Naoyuki Yoshida; Teruyo Sugiura; Kazutoshi Miyazawa; Yasuyuki Koizumi, all of Ichihara, Japan

[73] Assignee: Chisso Corporation, Osaka, Japan

[21] Appl. No.: 931,993

[22] Filed: Aug. 19, 1992

[30] Foreign Application Priority Data

Aug. 20, 1991 [JP] Japan .................. 3-231092
Feb. 10, 1992 [JP] Japan .................. 4-056600

[51] Int. Cl.$^5$ ............................. C07C 45/68
[52] U.S. Cl. ....................... 568/348; 568/354; 560/170; 560/120; 562/502
[58] Field of Search ............... 560/120, 170; 568/354, 568/348; 562/502

[56] References Cited

U.S. PATENT DOCUMENTS 3,679,756 7/1972 Kretschmar et al. ............... 560/120
3,813,438 5/1974 Oshima et al. ..................... 562/502

OTHER PUBLICATIONS

Wilberg, "Oxidation in Organic Chemistry", Part A, Ch. 1, p. 2, Academic Press.
Poll et al, Tetrahedron Lett., vol. 30, pp. 5595-5598 (1989).
Poll et al, Tetrahedron Lett., vol. 25, pp. 2191-2194 (1984).

Primary Examiner—James H. Reamer
Attorney, Agent, or Firm—Wenderoth, Lind & Ponack

[57] ABSTRACT

The present invention provides a method for producing optically active 3-substituted-2-norbornanones which are useful as starting materials for several kinds of physiologically active materials, and to their intermediates, optically active 2-hydroxy-2-norbornanecarboxylic acid and to a method for producing these intermediates.

3 Claims, No Drawings

METHOD FOR PRODUCING OPTICALLY ACTIVE 3-SUBSTITUTED-2-NORBORNANONES AND THEIR INTERMEDIATES

BACKGROUND OF THE INVENTION

1. Field of the Invention

The present invention relates to a method for producing optically active 3-substituted-2-norbornanones which are useful as starting materials for several kinds of physiologically active materials, and to the intermediates, optically active 2-hydroxy-2-norbornanecarboxylic acid and to a method for producing these intermediates. As an example, a thromboxane $A_2$ receptor antagonist useful as an anticoagulant can be synthesized from the above norbornanone. (Narisada et al., J. Med. Chem., 31, 1847(1988), Hamanaka et al., Tetrahedron Lett., 30, 2399(1989)).

2. Description of the Prior Art

Recently the synthesis of physiologically active materials as optically active compounds has become important. When a material has optical isomers, the activities are generally different among isomers. However, only one isomer usually shows strong activities and the other isomers show weak activities or undesired toxicity in many cases. Accordingly, when the plysiologically active materials are especially synthesized for medical supplies, it is required that desired optical isomers are selectively synthesized in order to develop sufficient physiological activities in safety.

To efficiently synthesize optically active 3-substituted-2-norbornanones of the present invention, it is necessary to efficiently obtain optically active 2-norbornanones. As for the synthesis of optically active 2-norbonanones, (1) a optical resolution method of racemic endo- or exo-2-norbornanol by using a diastereomer process (Winstein et al., J. Am. Chem. Soc., 74, 1147(1952), Berson et al., ibid., 83 3986(1961).), (2) a method of asymmetric oxidation or asymmetric reduction of racemic exo-2-norbornanol or 2-norbornanone with a horse liver alcohol dehydrogenase (Irwin et al., J. Am. Chem. Soc., 98, 8476(1976) and the like are reported. However, the method (1) is not efficient because recrystallization of the product should be repeated to improve the optical purity. The method (2) is not practical because a reagent to be used is expensive and the asymmetric yield of the product is low.

As described above, all of these cases are not satisfactory to practice on an industrial level.

For the above reasons, development of a simple process for producing optically active 3-substituted-2-norbornanone widely useful as synthetic intermediates of physiologically active materials has been long-desired.

SUMMARY OF THE INVENTION

The inventors of the present invention had a research for attaining an object to efficiently obtain a large amount of optically active 3-substituted-2-norbornanone, so that they found a production method for efficiently obtaining a large amount of optically active 3-substituted-2-norbornanones represented by the formula (II) below by using intermediates, such as optically active 2-hydroxy-2-norbornane carboxylic acids represented by the formula (III) below. The optically active 2-hydroxy-2-norbornane carboxylic acids are found by the inventors of the present invention, and these compounds are new. Although the synthesis of racemates of these compounds was reported (K. B. Wiberg (ed.), Oxidation in Organic Chemistry, Part A, Chapter I (page 2), Academic Press, New York/London), efficient synthesis of optically active compounds of the present invention which is industrially excellent is not yet known.

The present invention provides a method for producing an optically active 3-substituted-2-norbornanone represented by the formula:

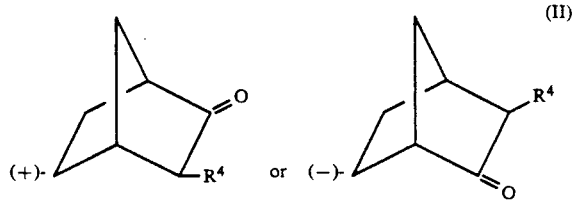

wherein $R^4$ is an alkyl, alkenyl, alkynyl, aryl or aralkyl group comprising reacting an optically active acrylic ester represented by the formula:

wherein $R^1$ is a member selected from the group consisting of

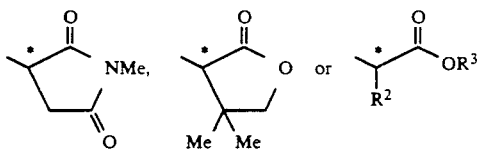

(wherein $R^2$ and $R^3$ are alkyl of 1–6 carbon atoms, cycloalkyl or aryl, respectively, or cyclic alkyl of 6 or less carbon atoms in combination, and * shows an asymmetric carbon) with cyclopentadiene, and applying the obtained compound to five steps consisting of hydrolysis, catalytic hydrogenation, oxidation, oxidative decarboxylation and alkylation.

Further, the present invention provides. method for producing an optically active 2-hydroxy-2-norbornane carboxylic acid represented by the formula:

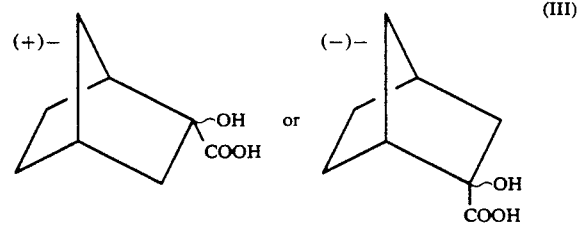

comprising reacting an optically active acrylic ester represented by the formula:

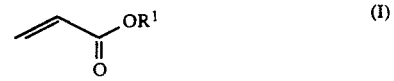

wherein $R^1$ is

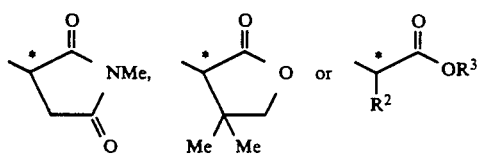

(wherein $R^2$ and $R^3$ are alkyl of 1–6 carbon atoms, cycloalkyl or aryl, respectively, or cyclic alkyl of 6 or less carbon atoms in combination, and * shows an asymmetric carbon) with cyclopentadiene, and applying the obtained compound to three steps consisting of hydrolysis, catalytic hydrogenation and oxidation. Further, the present invention provides the final product, namely, optically active 2-hydroxy-2-norbornane carboxylic acid.

In addition, the present invention provides an optically active 2-norbornanone represented by the formula:

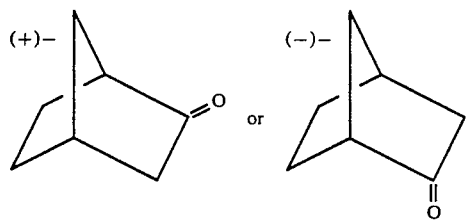

(IV)

which is obtained from an optically active 2-hydroxy-2-norbornane carboxylic acid represented by the formula:

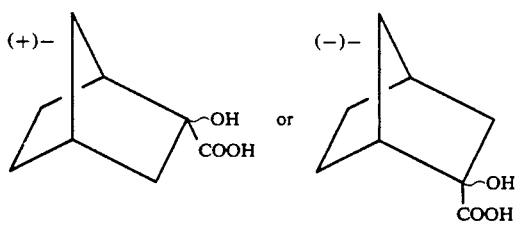

(III)

The method for producing the optically active compounds of the present invention is described in more detail below.

Optically active 3-substituted-2-norbornanone (II) of the present invention can be produced by the following reaction processes.

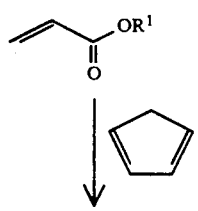

(I)

-continued

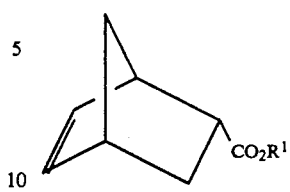

(V)

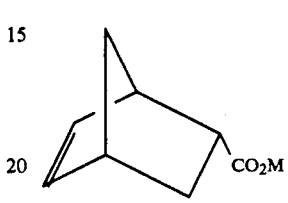

(VI)

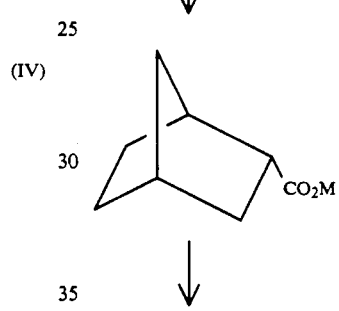

(VII)

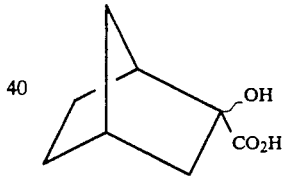

(III)

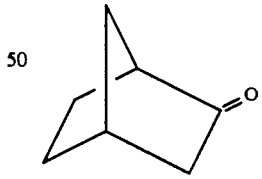

(IV)

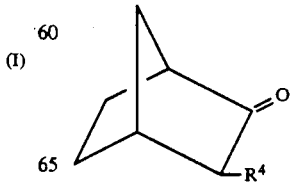

(II)

wherein $R^1$ is

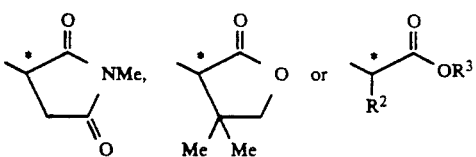

(wherein $R^2$ and $R^3$ are alkyl of 1-6 carbon atoms, cycloalkyl or aryl, respectively, or cyclic alkyl of 6 or less carbon atoms in combination, * shows an asymmetric carbon), $R^4$ is alkyl, alkenyl, alkynyl, aryl or aralkyl, and M is hydrogen or a metal atom selected from the group consisting of lithium, sodium, potassium and the like.

The starting compound (I) of the present invention having excellent optical purity can be obtained by a reaction of acrylic chloride with (S)-lactate, (R)-(−)-pantoyl lactone, (S)-(−)-N-methyl-2-hydroxysuccinimide or the like (Poll et al., Tetrahedron Lett., 25, 2191(1984); 30, 5595(1989).).

The compound (V) can be synthesized by a Diels-Alder reaction of cyclopentadiene with the compound represented by the formula (I) in the presence of a Lewis acid catalyst. As the catalyst used in the reaction, titanium tetrachloride can be exemplified. As a reaction solvent, a halogen type solvent such as methylene chloride, chloroform or dichloroethane or a mixture solvent of the halogen type solvent and a hydrocarbon type solvent such as pentane, hexane, heptane or petroleum ether can be used. The reaction temperature is suitably −78° C. to room temperature, especially preferably −20° to 0° C.

The compound represented by the formula (V) can be easily converted into the compound (VI) by hydrolysis under basic conditions.

Lithium hydroxide, sodium hydroxide and potassium hydroxide can be exemplified as the bases used in the reaction. An ether type solvent such as tetrahydrofuran, or a mixture solvent of the ether type solvent and an alcohol type solvent such as methanol, ethanol or solmix can be used as the reaction solvent. The reaction temperature is suitably 0° to 50° C., and especially preferably about 20° to 30° C.

The compound represented by the formula (VII) can be easily obtained by catalytic hydrogenation of the compound (VI). As the catalyst used in the reaction, palladium-carbon can be exemplified. Water, an alcohol type solvent such as methanol, ethanol or solmix, or a mixture thereof can be used as the reaction solvent. The reaction temperature is suitably 0° to 50° C., and preferably room temperature.

The compound represented by the formula (III) can be obtained by oxidizing the compound (VII). As the oxidizing agent used in the reaction, potassium permanganate can be exemplified. As the reaction solvent, water, or two phases of water and a hydrocarbon type solvent such as pentane, hexane, heptane or petroleum ether can be used. The reaction temperature is suitably 0° to 100° C., and especially preferably a temperature from room temperature to 70° C.

By the above operation, optically active 2-hydroxy-2-norbornanecarboxylic acid (III) can be prepared.

Moreover, the compound represented by the formula (IV) can be easily obtained by oxidizing the compound (III). As the oxidizing agent used in the reaction, sodium bismuthate-phosphoric acid, lead tetraacetate, chromic acid-sulfuric acid can be exemplified. These oxidizing agents can be used by a common method. As an example, when sodium bismuthate-phosphoric acid is used as the oxidizing agent, water may be used as a reaction solvent and the reaction temperature is preferably a temperature of from room temperature to 60° C.

The compound represented by the formula (II) can be easily obtained by enolization of the compound (IV) and then reaction with a halogenated alkyl. As the base used in the enolization, lithium diisopropyl amide (LDA) or lithium bis(trimethylsilyl)amide can be exemplified. As the halogenated alkyls, methyl chloride, methyl bromide, methyl iodide, allyl chloride, allyl bromide, allyl iodide, benzyl chloride, benzyl bromide, benzyl iodide, vinyl chloride, vinyl bromide, vinyl iodide, etc. can be exemplified. An ether type solvent such as tetrahydrofuran can be used as the reaction solvent. The reaction temperature is suitably −78° C. to room temperature, especially preferably −20° to 0° C.

By the above operation, optically active 3-substituted-2-norbornanone (II) can be prepared.

Typical compounds of obtained optically active 3-substituted-2-norbornanones are as follows:

(+)-3-methyl-2-norbornanone, (+)-3-ethyl-2-norbornanone, (+)-3-allyl-2-norbornanone, (+)-3-vinyl-2-norbornanone, (+)-3-benzyl-2-norbornanone, (+)-3-phenyl-2-norbornanone, (−)-3-methyl-2-norbornanone, (−)-3-ethyl-2-norbornanone, (−)-3-allyl-2-norbornanone, (−)-3-vinyl-2-norbornanone, (−)-3-benzyl-2-norbornanone, (−)-3-phenyl-2-norbornanone, etc.

Optically active 2-hydroxy-2-norbornane carboxylic acid of the present invention is a new compound which is firstly prepared by the inventors of the present invention. From the compound, a large amount of optically active 3-substituted-2-norbornanones which are useful for synthetic intermediates for physiologically active materials can be efficiently obtained. As an example, from optically active 3-allyl-2-norbornanone, thromboxane $A_2$ receptor antagonists (VIII) and (IX) useful for a blood coagulation inhibitor can be prepared via several steps. The (+)-type compound shows the highest activity. Concerning the compound (VIII), the activity of the racemate is one-third of that of the (+)-type compound and the activity of the (−)-type compound is only one-thirtieth of that of the (+)-type compound (Narisada et al., J. Med. Chem, 31, 1847(1988)). Accordingly, in order to obtain sufficient activity, it is essential to synthesize an optically active compound, especially a (+)-type compound. According to the present invention, (+)-3-allyl-2-norbornanone having high optical purity can be easily prepared with easily available asymmetric sources, low-priced materials and reagents.

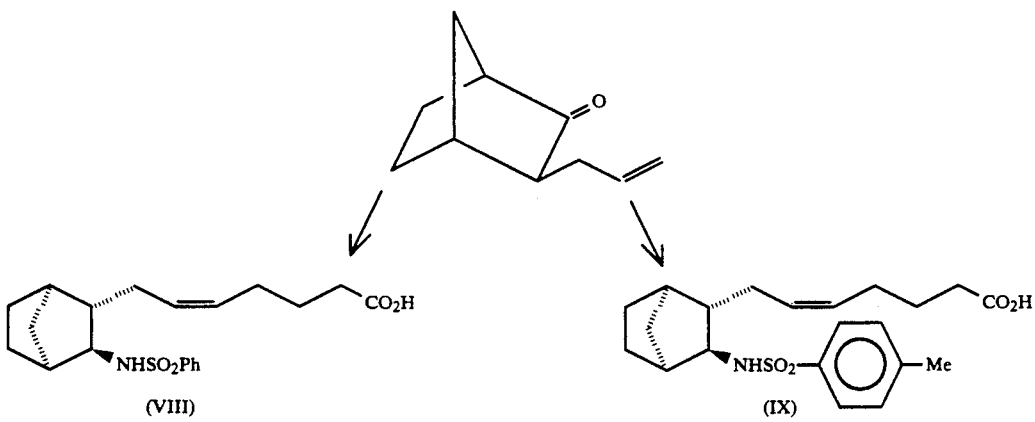

DESCRIPTION OF THE PREFERRED EMBODIMENTS

The following examples illustrate the present invention more specifically, but the present invention is not limited by these examples.

Example 1

Preparation of (+)-2-hydroxy-2-norbornanecarboxylic acid

Step 1

To a mixture of 69.5 g (538 mmol) of (S)-(−)-N-methyl-2-hydroxysuccinimide, 70.8 g (700 mmol) of triethylamine and 400 ml of methylene chloride, 63.4 g (700 mmol) of acryloyl chloride was dropwise added at a temperature of −25° C., and the mixture was stirred for 4.5 hours at −20° to −25° C. 170 ml of 1N hydrochloric acid was added to the reaction mixture on an ice bath to separate an organic layer and an aqueous layer, and the aqueous layer was extracted with methylene chloride (200 ml×3). After combining organic layers, the organic solution was washed with 150 ml of a saturated aqueous solution of sodium bicarbonate and then with 150 ml of a saturated aqueous solution of sodium chloride. After the organic solution was dried on anhydrous magnesium sulfate, the solvent was filtered off and 96.8g of crude acrylic acid ester was obtained.

The product was purified by silica gel chromatography (elution with ethyl acetate), and 72.2 g (394 mmol) of (S)-(−)-N-methyl-2-propenoyloxysuccinimide was obtained. Yield: 73%.

The compound was identified by $^1$H-NMR chart analysis. The data of $^1$H-NMR (CDCl$_3$) are shown in the following.

$^1$H-NMR: δ2.6–3.5 (m, 2H), 3.0 (s, 3H), 5.5–5.7 (m, 1H), 5.8–6.7 (m, 3H).

Step 2

72.2 g (394 mmol) of (S)-(−)-N-methyl-2-propenoyloxysuccinimide was dissolved in 580 ml of a mixture solvent of methylene chloride-petroleum ether (7:1), and 4.4 ml (40.1 mmol) of titanium tetrachloride in 30 ml of petroleum ether was added at −15° C. After the mixture was stirred at −10° to −15° C. for 30 minutes, 32.4 g (490 mmol) of cyclopentadiene prepared prior to the use was added dropwise and the mixture was stirred at the same temperature for 3.5 hours. After adding 50.1 g (175 mmol) of sodium carbonate 10 H$_2$O powder in limited amounts to the mixture, the temperature was slowly raised to room temperature, and the mixture was stirred for one hour. Insoluble materials were filtered and washed with methylene chloride (250 ml×3). The filtrate and the washed liquid were distilled off, and 99.6 g of crude Diels-Alder adduct was obtained. The adduct was recrystallized from 600 ml of a mixture solvent of heptane-ethyl acetate (5:3) to obtain 67.0 g (269 mmol) of a purified Diels-Alder adduct. Yield: 68%.

The compound was identified by $^1$H-NMR chart analysis. The data of $^1$H-NMR (CDCl$_3$) are shown in the following.

$^1$H-NMR: δ1.2–2.2 (m, 4H), 2.4–3.4 (m, 5H), 3.0 (s, 3H), 5.3–5.5 (m, 1H), 5.8–6.0 (m, 1H), 6.1–6.3 (m, 1H).

Further, the physical property values are as follows.
Melting point: 134.9°–136.6° C.
Specific rotation: +85.2° (c 1.037, CHCl$_3$).

Step 3

67.0 g (269 mmol) of the Diels-Alder adduct was dissolved in 1040 ml of a mixture solvent of tetrahydrofuran-water (5:2), 70.5 g (1.08 mol) of potassium hydroxide (85%) in 300 ml of water was added on ice cooling, and the mixture was stirred at room temperature for 24 hours. After distilling out tetrahydrofuran, the product was neutralized with 94 ml of concentrated hydrochloric acid and extracted with a mixture solvent of hexane-methylene chloride (98:2) (200 ml×4). The extract was dried on anhydrous magnesium sulfate, the solution was filtered, and the solvent was distilled off to obtain 38.8 g of crude 5-norbornene-2-carboxylic acid. Crude yield: 100%.

The product was identified by $^1$H-NMR chart analysis. The data of $^1$H-NMR (CDCl$_3$) are shown in the following:

$^1$H-NMR: δ1.1–1.6 (m, 3H), 1.7–2.1 (m, 1H), 2.7–3.3 (m, 3H), 6.0 (dd, 1H), 6.2 (dd, 1H), 11.4 (brs, 1H).

Further, a part of the product was purified by distillation. The physical property values are as follows:
Melting point: 84° C./1 mmHg
Specific rotation: +142.0° (c 5.02, EtOH).

Step 4

38.8 g (269 mmol) of crude 5-norbornene-2-carboxylic acid was dissolved in 740 ml of solmix, 1.92 g of 5% palladium-carbon powder was added and the mixture was stirred for 17.5 hours under an atmosphere of hydrogen. The catalyst was filtered off, the solvent was distilled away, and 38.0 g of crude 2-norbornanecarboxylic acid was obtained. Crude yield: 100%.

The compound was identified by $^1$H-NMR chart analysis. The data of $^1$H-NMR (CDCl$_3$) are shown in the following $^1$H-NMR: δ1.1–1.9 (m, 8H), 2.2–2.4 (m, 1H), 2.5–3.0 (m, 2H), 11.0 (brs, 1H).

Further, a part of the product was purified by distillation. The physical property values are as follows:
Boiling point: 96° C./2 mmHg
Specific rotation: +38.5° (c 1.933, CHCl3).

Step 5

107 g (1.63 mol) of potassium hydroxide (85%) and 85.7 g (542 mmol) of potassium permanganate were dissolved in 380 ml of water, and 37.9 g (271 mmol) of crude 2-norbornanecarboxylic acid in 380 ml of petroleum ether was added dropwise on ice cooling. After heating and refluxing for eight hours, the mixture was stirred at room temperature for 18 hours. The reaction mixture was slowly added to 544 ml of 6N sulfuric acid, to obtain acidified mixture, then 272 ml of an aqueous solution of 62.2 g of sodium bisulfite was added, and the mixture was stirred at room temperature for one hour. After the reaction mixture was extracted with ethyl acetate (200 ml×4), the extract was dried over anhydrous magnesium sulfate. The extract was filtered, the solvent was distilled off and 38.5 g of crude 2-hydroxy-2-norbornanecarboxylic acid was obtained. Crude yield: 92%.

The compound was identified by $^1$H-NMR chart analysis. The data of $^1$H-NMR (CDCl$_3$) are shown in the following.

$^1$H-NMR: δ1.0–2.3 (m, 10H), 7.4 (brs, 2H).
Further, the physical property values are as follows:
Melting point: 90°–94° C.
Specific rotation: +27.7° (c 1.076, EtOH).

Example 2

Production of (+)-2-hydroxy-2-norbornanecarboxylic acid

Step 1

5.00 g (20.0 mmol) of the Diels-Alder adduct obtained in Step 2 of Example 1 was suspended in 40 ml of a mixture solvent of tetrahydrofuran-methanol (1:1), 1.86 g (43.3 mmol) of sodium hydroxide (93%) in 4 ml of water was added, and the mixture was stirred for 24 hours. Then, 280 mg of 5% palladium-carbon powder was added, and the mixture was stirred for 5 hours under an atmosphere of hydrogen. The catalyst was filtered off, the solvent was distilled off, and the residue was diluted with water. The solution was acidified with concentrated hydrochloric acid and extracted with a mixture solvent of hexane-methylene chloride (98:2) (50 ml×4). The extract was dried over anhydrous magnesium sulfate and filtered, the solvent was distilled off, and 2.67 g of crude 2-norbornanecarboxylic acid was obtained. Crude yield: 95%.

The compound was identified by $^1$H-NMR chart analysis.

Step 2

9.59 g (68.4 mmol) of crude 2-norbornanecarboxylic acid obtained by the above step was dissolved in 50 ml of water, 4.55 g (68.9 mmol) of potassium hydroxide (85%) was added on ice cooling, and the mixture was stirred for six hours. The reaction solution was added dropwise in a mixture of 30.0 g (456 mmol) of potassium hydroxide (85%), 23.4 g (148 mmol) of potassium permanganate and 50 ml of water. After heating and stirring at 40°–50° C. for nine hours, the mixture was stirred at room temperature for 18 hours. The product was treated by the same method as described in Step 5 of Example 1, and 9.51 g of crude 2-hydroxy-2-norbornanecarboxylic acid was obtained. Crude yield: 89%.

The compound was identified by $^1$H-NMR chart analysis.

Example 3

Production of (+)-2-hydroxy-2-norbornanecarboxylic acid

Step 1

5.00 g (20.0 mmol) of the Diels-Alder adduct obtained by the step 2 of Example 1 was dissolved in 45 ml of a mixture solvent of tetrahydrofuran-water (5:4), 1.85 g (43.0 mmol) of sodium hydroxide (93%) was added on ice cooling, and the mixture was stirred at room temperature for 24 hours. After tetrahydrofuran was distilled off, the reaction mixture was neutralized with concentrated hydrochloric acid. Then, 280 mg of 5% palladium-carbon powder was added and the mixture was stirred for 30 hours under an atmosphere of hydrogen. The catalyst was filtered off, the filtrate was acidified with concentrated hydrochloric acid and extracted with a mixture solvent of hexane-methylene chloride (98:2) (50 ml×4). The extract was dried over anhydrous magnesium sulfate and filtered, the solvent was distilled off, and 2.66 g of crude 2-norbornanecarboxylic acid was obtained. Crude yield: 95%.

The compound was identified by $^1$H-NMR chart analysis.

Step 2

1.83 g (13.1 mmol) of crude 2-norbornanecarboxylic acid obtained by the above step was dissolved in 10 ml of water, 0.87 g (13.1 mmol) of potassium hydroxide (85%) was added on ice cooling, and the mixture was stirred for six hours. The reaction solution was added dropwise in a mixture of 5.22 g (79.5 mmol) of potassium hydroxide (85%), 4.57 g (28.9 mmol) of potassium permanganate, 10 ml of water and 20 ml of hexane. After heating and stirring at 40°–50° C. for eight hours, the mixture was stirred at room temperature for 18 hours. The product was treated by the same method as described in Step 5 of Example 1, and 1.74 g of crude 2-hydroxy-2-norbornanecarboxylic acid was obtained. Crude yield: 85%.

The compound was identified by $^1$H-NMR chart analysis.

Example 4

Production of (+)-5-norbornene-2-carboxylic acid

Step 1

To a mixture of 59.0 g 499 mmol) of (S)-(−)-ethyl lactate, 55.7 g (550 mmol) of triethylamine and 200 ml of methylene chloride, 49.8 g (550 mmol) of acryloyl chloride in 100 ml of dichloroethane was added dropwise at a temperature of −20° C., and the mixture was stirred at −20° C. for 4.5 hours. On ice cooling, the reaction mixture was separated into an organic layer by adding 1N hydrochloric acid, and an aqueous layer was extracted with methylene chloride. Organic layers were combined, and washed with successive, saturated sodium bicarbonate solution, water, and saturated sodium chloride solution.

The product solution was dried over anhydrous magnesium sulfate and filtered, the solvent was distilled off, and 75.0 g of crude (S)-ethyl 2-propenoyloxypropionate was obtained.

The compound was identified by $^1$H-NMR chart analysis. The data of $^1$H-NMR (CDCl$_3$) are shown in the following.

$^1$H-NMR: δ1.3 (t, 3H), 1.5 (d, 3H), 4.2 (q, 2H), 5.1 (q, 1H), 5.8–6.6 (m, 3H).

Further, a part of the product was purified by distillation. The physical property values are as follows:
Boiling point: 68° C./8 mmHg
Specific rotation: −38° c 2.1, CHCl$_3$).

Step 2

67.5 g (382 mmol) of crude (S)-ethyl 2-propenoyloxypropionate was dissolved in 150 ml of methylene chloride, and 5.0 ml (45.6 mmol) of titanium tetrachloride in 30 ml of hexane was added at a temperature of −20° C. The mixture was stirred at −10° C. for 30 minutes, 31.1 g (470 mmol) of cyclopentadiene in 50 ml of methylene chloride which was prepared just prior to the use was added dropwise, and the mixture was stirred at the same temperature for two hours. After adding 20.0 g (69.9 mmol) of sodium carbonate 10 H$_2$O powder in limited amounts, the temperature of the mixture was slowly raised to room temperature, and the mixture was stirred overnight. Insoluble materials were filtered and washed with methylene chloride. The filtrate and the washed liquid were combined, and the solution was washed with successive, saturated sodium bicarbonate, and water. The solution was dried over magnesium sulfate and filtered, the solvent was distilled off, and 95.0 g of crude Diels-Alder adduct was quantitatively obtained.

The compound was identified by $^1$H-NMR chart analysis. The data of $^1$H-NMR (CDCl$_3$) are shown in the following.

$^1$H-NMR: δ1.2–1.5 (m, 10H), 2.6–3.1 (m, 3H), 4.3 (q, 2H), 5.1 (q, 1H), 6.0–6.2 (m, 2H).

Step 3

95.0 g (382 mmol) of the Diels-Alder adduct obtained in the above step was dissolved in 950 ml of tetrahydrofuran, 103 g (1.57 mol) of potassium hydroxide (85%) in 760 ml of water was added on ice cooling, and the mixture was stirred at room temperature for 24 hours. After tetrahydrofuran was distilled off from the reaction mixture, the residue was neutralized with 138 ml of concentrated hydrochloric acid, and the solution was extracted with a mixture solvent of hexane-methylene chloride (98:2) (200 ml×4). The extract was dried over anhydrous magnesium sulfate and filtered, the distilled off, and 45.0 g of crude 5-norbornene-2-carboxylic acid was obtained. Crude yield: 83%.

The compound was identified by $^1$H-NMR chart analysis.

Further, the steric configuration of the compound was a (+)-compound by the sign of the optical rotation.

Example 5

Production of (+)-5-norbornene-2-carboxylic acid

Step 1

To a mixture of 10.1 g (58.5 mmol) of cyclohexyl (s)-(−)-lactate, 8.1 g (80.4 mmol) of triethylamine and ml of methylene chloride, 5.7 ml (70.2 mmol) of acryloyl chloride was added dropwise at a temperature of −20° C., and the mixture was stirred at −20° C. for 5.5 hours. On ice cooling, 1N hydrochloric acid was added to the reaction mixture to separate an organic layer, and an aqueous layer was extracted with methylene chloride. Organic layers were combined and washed with successive, saturated sodium bicarbonate solution, water, and saturated sodium chloride solution. The solution was dried over anhydrous magnesium sulfate and filtered, the solvent was distilled off, and 13.5 g of crude (S)-cyclohexyl 2-propenoyloxypropionate was obtained.

The compound was identified by $^1$H-NMR chart analysis. The data of $^1$H-NMR (CDCl$_3$) are shown in the following.

$^1$H-NMR: δ1.1–2.2 (m, 10H), 1.5 (d, 3H), 4.7–5.0 (m, 1H), 5.1 (q, 1H), 5.8–6.6 (m, 3H).

Step 2

13.5 g (58.5 mmol) of crude (S)-cyclohexyl 2-propenoyloxypropionate was dissolved in 60 ml of a mixture solvent of methylene chloride-hexane (5:1), and 0.7 ml (6.4 mmol) of titanium tetrachloride was added at a temperature of −20° C. The mixture was stirred at −10° C. for 30 minutes, 6.1 g (92.6 mmol) of cyclopentadiene prepared just prior to the use was added dropwise, and the mixture was stirred at the same temperature for 4.5 hours. After adding 8.1 g (28.4 mmol) of sodium carbonate 10 H$_2$O powder in limited amounts to the mixture, the temperature was slowly raised, and the mixture was stirred at room temperature overnight. Insoluble materials were filtered and washed with methylene chloride. The filtrate and the washed liquid were combined, and the solution was washed with successive, saturated sodium carbonate, and water. The solution was dried over anhydrous magnesium sulfate and filtered, the solvent was distilled off, and 19.1 g of crude Diels-Alder adduct was quantitatively obtained.

The compound was identified by $^1$H-NMR chart analysis. The data of $^1$H-NMR (CDCl$_3$) are shown in the following.

$^1$H-NMR: δ1.1–2.2 (m, 14H), 1.5 (d, 3H), 2.6–3.4 (m, 3H), 4.2–5.0 (m, 1H), 5.0 (q, 1H), 5.8–6.3 (m, 2H).

Step 3

19.0 g (58.5 mmol) of the Diels-Alder adduct was dissolved in 115 ml of tetrahydrofuran, 12.9 g (300 mmol) of sodium hydroxide in 140 ml of water was added on ice cooling, the mixture was stirred at room temperature for 24 hours. After distilling off tetrahydrofuran, the product was neutralized with 27 ml of concentrated hydrochloric acid and extracted with a mixture solvent of hexane-methylene chloride (98:2) (100 ml×4). The extract was dried over anhydrous magnesium sulfate, the solution was filtered, and the solvent was distilled off to obtain 8.3 g of crude 5-norbornene-2-carboxylic acid.

The compound was identified by $^1$H-NMR chart analysis.

Further, the steric configuration of the compound was a (+)-compound by the sign of the optical rotation.

Example 6

Production of (+)-exo-3-allyl-2-norbornanone

Step 1

38.5 g (247 mmol) of crude 2-hydroxy-2-norbornanecarboxylic acid and 90.6 g (259 mmol) of sodium bismuthate (80%) were dissolved in 400 ml of water, 83.9 g (728 mmol) of phospholic acid (85%) was added dropwise, and the mixture was stirred at 45° to 50° C. for six hours and then at room temperature for 18 hours. The reaction mixture was extracted with ethyl acetate (200 ml×4), and the extract was washed with successive, saturated sodium bicarbonate solution, water and saturated sodium chloride solution (each 200 ml), and dried over anhydrous magnesium sulfate. After ethyl acetate was distilled off at atmospheric pressure, and the residue was distilled to obtain 14.8 g (134 mmol) of (+)-2-norbornanone. Yield 50%.

The compound was identified by $^1$H-NMR chart analysis The data of $^1$H-NMR (CDCl$_3$) are shown in the following.

$^1$H-NMR: $\delta$1.2-2.3 (m, 8H), 2.5-2.9 m, (2H).

Further, the physical property values are as follows:
Boiling point: 174° C.
Specific rotation: +29.0° (c 1.51, CHCl$_3$).

Step 2

To 194 ml (388 mmol) of a 2M solution of lithium diisopropyl amide in tetrahydrofuran-hexane, 50 ml of a solution of 38.9 g (353 mmol) of (+)-2-norbornanone in tetrahydrofuran was added dropwise at −40° C., and the mixture was stirred at −20° C. for 30 minutes. Then, 30 ml of a solution of 47.0 g (388 mmol) of allyl bromide in tetrahydrofuran was added dropwise, the mixture was stirred at −20° C. for 30 minutes, the temperature of the mixture was raised to room temperature, and the mixture was stirred for one hour. On ice cooling, the reaction mixture was poured into 300 ml of 2N hydrochloric acid, and the mixture was extracted with toluene (200 ml×4). The extract was washed with successive, saturated sodium bicarbonate solution, water, saturated sodium chloride (each 200 ml), and dried over anhydrous magnesium sulfate. The solution was filtered, and the solvent was distilled off to obtain 77.6 g of crude 3-allyl-2-norbornanone. The crude product was purified by distillation, and 42.5 g (134 mmol) of (+)-exo-3-allyl-2-norbornanone was obtained. Yield: 80%.

The compound was identified by $^1$H-NMR chart analysis. The data of $^1$H-NMR (CDCl$_3$) are shown in the following.

$^1$H-NMR: $\delta$1.2-2.8 (m, 11H), 4.9-5.3 (m, 2H), 5.6-6.1 (m, 1H).

Further, the physical property values are as follows:
Boiling point: 71°-72.5° C./3 mmHg
Specific rotation: +87.3° (c 1.08, CHCl$_3$).

Example 7

Production of (−)-2-hydroxy-2-norbornanecarboxylic acid

Step 1

To a mixture of 46.8 g (360 mmol) of (R)-(−)-pantoyllactone, 54.7 g (541 mmol) of triethylamine and 300 ml of methylene chloride, 41.2 g (455 mmol) of acryloyl chloride was added dropwise at −25° C., and the mixture was stirred at −20° to −25° C. for five hours. On ice cooling, 500 ml of 0.5N hydrochloric acid was added to the reaction mixture to separate an organic layer, and an aqueous layer was extracted with methylene chloride (150 ml×3). Organic layers were combined and washed with successive, saturated sodium bicarbonate solution, water, and saturated sodium chloride solution (each 250 ml). The solution was dried over magnesium sulfate and filtered, and the solvent was distilled off to obtain 64.5 g of crude acrylic acid ester. The product was purified by silica gel column chromatography (hexane-ethyl acetate 3:1), and 61.3 g (333 mmol) of (R)-dihydro-3-propenoyloxy-4,4-dimethyl-2(3H)-furanone was obtained. Yield: 93%.

The compound was identified by $^1$H-NMR chart analysis. The data of $^1$H-NMR (CDCl$_3$) are shown in the following.

$^1$H-NMR: $\delta$1.1 (s, 3H), 1.3 (s, 3H), 4.0 (s, 2H), 5.5 (s, 1H), 5.9-6.7 (m, 3H).

Step 2

25.1 g (136 mmol) of (R)-dihydro-3-propenoyloxy-4,4-dimethyl-2(3H)-furanone was dissolved in 200 ml of a mixture solvent of methylene chloride-petroleum ether (7:1), and 1.6 ml (14.6 mmol) of titanium tetrachloride was added at −15° C. The mixture was stirred at −10° to −15° C. for 30 minutes, 11.9 g (180 mmol) of cyclopentadiene prepared just prior to the use was added dropwise to the mixture, and the mixture was stirred at the same temperature for three hours. After adding 17.3 g (60.4 mmol) of sodium carbonate 10 H$_2$O powder in limited amounts to the reaction mixture, the temperature was slowly raised, and the mixture was stirred at room temperature for 30 minutes. Insoluble materials were filtered and washed with methylene chloride (100 ml×3). The filtrate and the washed liquid were combined and distilled off to obtaine 34.0 g of crude Diels-Alder adduct was obtained. The crude product was recrystallized from 125 ml of a mixture solvent of heptane-ethyl acetate (5:3) to obtain 27.5 g (110 mmol) of a pure product. Yield: 81%.

The compound was identified by $^1$H-NMR chart analysis. The data of $^1$H-NMR (CDCl$_3$) are shown in the following:

$^1$H-NMR: $\delta$1.0-2.2 (m, 4H), 1.1 (s, 3H), 1.2 (s, 3H), 2.8-3.3 (m, 3H), 4.0 (s, 2H), 5.3 (m, 1H), 5.8-6.0 (m, 1H), 6.2-6.4 (m, 1H).

Further, the physical property value is as follows:
Melting point: 114°-115° C.

Step 3

27.5 g (110 mmol) of the Diels-Alder adduct obtained in the above step was dissolved in 420 ml of a mixture solvent of tetrahydrofuran-water (5:2), on ice cooling, 30.0 g (455 mmol) of potassium hydroxide (85%) in 120 ml of water was added, and the mixture was stirred at room temperature for 24 hours. After distilling off tetrahydrofuran, the residue was neutralized with 40 ml of concentrated hydrochloric acid, and the solution was extracted with a mixture solvent of hexane-methylene chloride (98:2) (150 ml×4). The extract was dried over anhydrous magnesium sulfate and filtered, the solvent was distilled off, and 15.7 g of crude 5-norbornene-2-carboxylic acid was obtained. Crude yield: 100%.

The compound was identified by $^1$H-NMR chart analysis. The data of $^1$H-NMR (CDCl$_3$) are shown in the following:

$^1$H-NMR: $\delta$1.1-1.6 (m, 3H), 1.7-2.1 (m, 1H), 2.7-3.3 (m, 3H), 6.0 (dd, 1H), 6.2 (dd, 1H), 11.4 (brs, 1H).

Step 4

15.7 g (110 mmol) of crude 5-norbornene-2-carboxylic acid was dissolved in 300 ml of ethanol, 1.55 g of 5% palladium-carbon powder was added, and the mixture was stirred under an atmosphere of hydrogen for 24 hours. After the catalyst was filtered off, the solvent was distilled off, and 14.5 g of crude 2-norbornanecarboxylic acid was obtained. Crude yield: 94%.

The compound was identified by $^1$H-NMR chart analysis. The data of $^1$H-NMR (CDCl$_3$) are shown in the following.

$^1$H-NMR: δ1.1-1.9 (m, 8H), 2.2-2.4 (m, 1H), 2.5-3.0 (m, 2H), 11.0 (brs, 1H).

Step 5

24.1 g (367 mmol) of potassium hydroxide (85%) and 18.9 g (120 mmol) of potassium permanganate were dissolved in 84 ml of water, on ice cooling, 8.36 g (59.6 mmol) of crude 2-norbornane carboxylic acid in 84 ml of petroleum ether was added dropwise. After heating and refluxing for six hours, the mixture was stirred at room temperature for 18 hours. On ice cooling, the reaction mixture was slowly added into 120 ml of 6N sulfuric acid, 60 ml of an aqueous solution of 13.0 g of sodium bisulfite was added to the acid mixture, and the solution was stirred at room temperature for one hour. The solution was extracted with ether (100 ml×4), and the extract was dried over anhydrous magnesium sulfate and filtered. The solvent was distilled off, and 8.34 g of crude 2-hydroxy-2-norbornanecarboxylic acid was obtained. Crude yield: 90%.

The compound was identified by $^1$H-NMR chart analysis. The data of $^1$H-NMR (CDCl$_3$) are shown in the following.

$^1$H-NMR: δ1.0-2.3 (m, 10H), 7.4 (brs, 2H).

Example 8

Production of (−)-exo-3-allyl-2-norbornanone

Step 1

8.25 g (52.8 mmol) of crude 2-hydroxy-2-norbornanecarboxylic acid and 19.5 g (55.7 mmol) of sodium bismuthate (80%) were dissolved in 85 ml of water, 18.0 g (156 mmol) of phospholic acid (85%) was added dropwise, and the mixture was stirred at 40° to 50° C. for eight hours and then at room temperature for 18 hours. The reaction mixture was extracted with ether (100 ml×4), and the extract was washed with successive, saturated sodium bicarbonate solution, water and saturated sodium chloride solution (each 100 ml), and dried over anhydrous magnesium sulfate. After ether was distilled off at atmospheric pressure, and the residue was distilled to obtain 3.09 g (28.1 mmol) of (−)-2-norbornanone. Yield 53%.

The compound was identified by $^1$H-NMR chart analysis The data of $^1$H-NMR (CDCl$_3$) are shown in the following.

$^1$H-NMR: δ1.2-2.3 (m, 8H), 2.5-2.9 (m, 2H).

Further, the physical property values are as follows:
Boiling point: 174° C.
Specific rotation: −28.5° (c 1.55, CHCl$_3$).

Step 2

To 3.4 ml (6.8 mmol) of a 2M solution of lithium diisopropyl amide in tetrahydrofuran-hexane, 1 ml of a solution of 500 mg (4.54 mmol) of (−)-2-norbornanone in tetrahydrofuran was added dropwise at −40° C., and the mixture was stirred at −20° C. for 10 minutes. Then, 1 ml of a solution of 540 mg (4.46 mmol) of allyl bromide in tetrahydrofuran was added dropwise, the mixture was stirred at −20° C. for 30 minutes, the temperature of the mixture was raised to room temperature, and the mixture was stirred for one hour. On ice cooling, the reaction mixture was poured into 20 ml of 1N hydrochloric acid, and the mixture was extracted with toluene (50 ml×4). The extract was washed with successive, saturated sodium bicarbonate solution, water, saturated sodium chloride (each 50 ml), and dried over anhydrous magnesium sulfate. The solution was filtered, and the solvent was distilled off to obtain 980 mg of crude 3-allyl-2-norbornanone. The product was purified by distillation, and 550 mg (3.66 mmol) of (−)-exo-3-allyl-2-norbornanone was obtained. Yield: 81%.

The compound was identified by $^1$H-NMR chart analysis. The data of $^1$H-NMR (CDCl$_3$) are shown in the following.

$^1$H-NMR: δ1.2-2.8 (m, 11H), 4.9-5.3 (m, 2H), 5.6-6.1 (m, 1H).

Further, the physical property values are as follows:
Boiling point: 70°-73° C./3 mmHg
Specific rotation: −89.1° (c 0.972, CHCl$_3$).

We claim:

1. A method for producing an optically active 3-substituted-2-norbornanone represented by the formula:

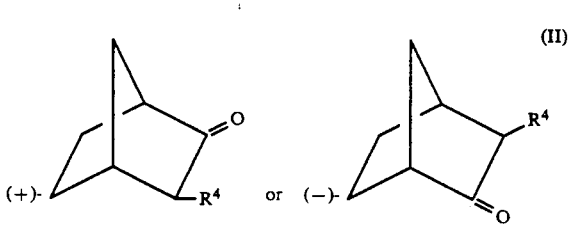

wherein R$^4$ is an alkyl, alkenyl, alkynyl, aryl or aralkyl group comprising (1) reacting an optically active acrylic ester represented by the formula:

wherein R$^1$ is a member selected from the group consisting of

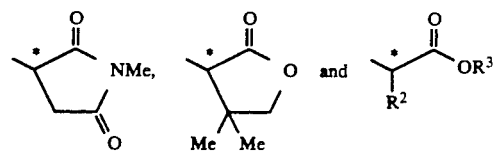

wherein R$^2$ and R$^3$ are alkyl of 1-6 carbon atoms, cycloalkyl or aryl, respectively, or cyclic alkyl of 6 or less carbon atoms in combination, and * shows an asymmetric carbon with cyclopentadiene in the presence of a Lewis acid catalyst and a solvent at a temperature of from −78° C. to room temperature to obtain a Diels-Alder adduct, (2) subjecting the Diels-Alder adduct of step (1) to hydrolysis under basic conditions at a temperature of 0° to 50° C. in a solvent to obtain a compound of the formula

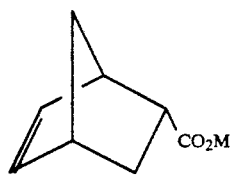

wherein M is hydrogen or a metal selected from the group consisting of lithium, sodium or potassium (3) subjecting the compound of the formula (VI) to catalytic hydrogenation with a hydrogenation catalyst in a solvent at a temperature of 0° to 50° C. to obtain a compound of the formula

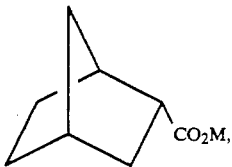

(4) oxidizing the compound of formula (VII) with an oxidizing agent at a temperature of 0° to 100° C. in a solvent to obtain a compound of the formula

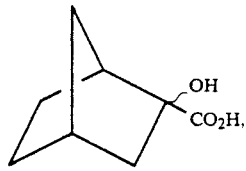

(5) subjecting the compound of formula (III) to oxidative decarboxylation with an oxidizing agent in a solvent at a temperature of from room temperature to 60° C. to obtain a compound of the formula

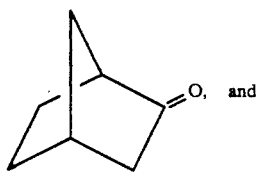

(6) subjecting the compound of the formula IV to enolization by treatment with a base and to subsequent alkylation with a halogenated alkyl the reactions being conducted in a solvent at a temperature of −78° C. to room temperature.

2. A method for producing an optically active 2-hydroxy-2-norbornane carboxylic acid represented by the formula:

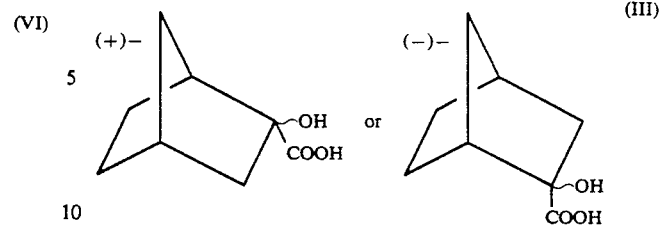

comprising reacting an optically active acrylic ester represented by the formula:

wherein $R^1$ is

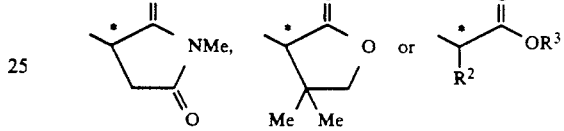

wherein $R^2$ and $R^3$ are alkyl of 1–6 carbon atoms, cycloalkyl or aryl, respectively, or cyclic alkyl of 6 or less carbon atoms in combination, and * shows an asymmetric carbon with cyclopentadiene in the presence of a Lewis acid catalyst and a solvent at a temperature of from −78° C. to room temperature to obtain a Diels-Alder adduct, (2) subjecting the Diels-Alder adduct of step (1) to hydrolysis under basic conditions at a temperature of 0° to 50° C. in a solvent to obtain a compound of the formula

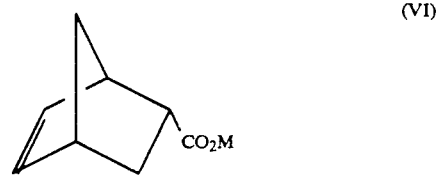

wherein M is hydrogen or a metal selected from the group consisting of lithium, sodium or potassium (3) subjecting the compound of the formula (VI) to catalytic hydrogenation with a hydrogenation catalyst in a solvent at a temperature of 0° to 50° C. to obtain a compound of the formula

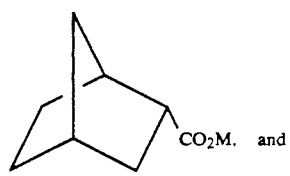

(4) oxidizing the compound of formula (VII) with an oxidizing agent at a temperature of 0° to 100° C. in a solvent to obtain a compound of the formula 3. A method for producing an optically active 3-substituted-2-norbornanone comprising subjecting an optically active 2-hydroxy-2-norbornanecarboxylic acid represented by the formula:

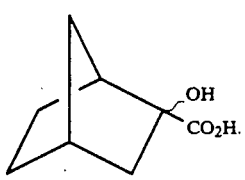

(III)

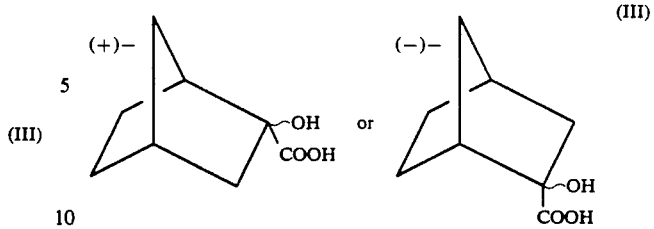

to oxidative decarboxylation with an oxidizing agent in a solvent at a temperature of from room temperature to 60° C. to obtain an optically active 2-norbornanone represented by the formula:

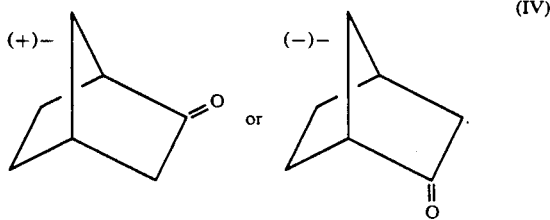

(IV)

* * * * *